(12) United States Patent
Cordero Marcos et al.

(10) Patent No.: US 10,981,019 B2
(45) Date of Patent: Apr. 20, 2021

(54) SYSTEMS AND METHODS FOR TRIGGERING ADAPTIVE PLANNING USING KNOWLEDGE BASED MODEL

(71) Applicant: Varian Medical Systems International AG, Cham (CH)

(72) Inventors: María Isabel Cordero Marcos, Espoo (FI); Hannu Mikael Laaksonen, Espoo (FI); Esa Kuusela, Helsinki (FI)

(73) Assignee: Varian Medical Systems International AG

( * ) Notice: Subject to any disclaimer, the term of this patent is extended or adjusted under 35 U.S.C. 154(b) by 449 days.

(21) Appl. No.: 15/886,373

(22) Filed: Feb. 1, 2018

(65) Prior Publication Data
US 2019/0232087 A1  Aug. 1, 2019

(51) Int. Cl.
*A61N 5/10* (2006.01)
*G16H 50/20* (2018.01)
*G16H 50/50* (2018.01)

(52) U.S. Cl.
CPC ......... *A61N 5/1038* (2013.01); *A61N 5/1039* (2013.01); *A61N 5/1049* (2013.01); *G16H 50/20* (2018.01); *G16H 50/50* (2018.01)

(58) Field of Classification Search
CPC ............................. A61N 5/1038; A61N 5/1039
USPC .......................................................... 600/1–8
See application file for complete search history.

(56) References Cited

U.S. PATENT DOCUMENTS

| | | | |
|---|---|---|---|
| 9,764,162 B1 * | 9/2017 | Willcut | A61B 5/743 |
| 2009/0257557 A1 * | 10/2009 | Sumanaweera | A61N 5/1049 378/65 |
| 2016/0310761 A1 | 10/2016 | Li et al. | |

FOREIGN PATENT DOCUMENTS

| | | |
|---|---|---|
| CN | 104258507 A | 1/2015 |
| CN | 106110520 A | 11/2016 |

OTHER PUBLICATIONS

European Search Report dated Jul. 2, 2019 for corresponding EP Patent Application No. 19155097.9.

* cited by examiner

*Primary Examiner* — John P Lacyk
(74) *Attorney, Agent, or Firm* — Vista IP Law Group, LLP

(57) ABSTRACT

An apparatus includes: one or more input communicatively coupled to one or more medium storing current treatment plan data and a current image of a patient, the one or more input configured to obtain the current treatment plan data and the current image of the patient, wherein the current treatment plan data is for processing by a treatment machine; and a re-planning decision processor configured to determine a re-plan information based at least in part on the current treatment plan data, the current image, and a re-plan triggering model, the re-plan triggering model based on previous treatment plan data and previous image(s), wherein the re-plan information indicates a recommendation regarding treatment re-planning; wherein the re-planning decision processor is configured to output the re-plan information for reducing a burden, or for obviating a need, for a user of the apparatus to manually decide whether the treatment re-planning is desirable or not.

21 Claims, 11 Drawing Sheets

SYSTEMS AND METHODS FOR TRIGGERING ADAPTIVE PLANNING USING KNOWLEDGE BASED MODEL

FIELD

An embodiment described herein relates to system and method for triggering adaptive planning using knowledge based model.

BACKGROUND

In radiotherapy treatment, the goal is to deliver a high dose to the cancer area (to kill the tumor cells) while sparing the healthy tissue (especially critical organs). A radiotherapy treatment may include multiple fractions, and it is critical that the radiation is delivered to the correct spot in all of the fractions. However, the daily situation at the time of treatment delivery might differ considerably from the situation predicted in the treatment plan, due to, for examples, internal organ movement (e.g., bladder filling, bowel movement, etc.), patient weight loss, tumor shrinkage, etc. In certain occasions, if the difference between the actual situation at the time of treatment delivery and the predicted situation in the treatment plan is too great, the goal of the treatment may no longer be met. In such cases, a new treatment plan is needed. This is known as adaptive radiotherapy (ART).

The problem with ART is that currently it is not clear when a new treatment plan is needed. Performing a new plan for every treatment fraction is not always desirable as it is a time consuming task for both staff and patient. Moreover, in some cases, the patient geometry has not changed sufficiently to justify a determination of a new treatment plan. Also, a change in the patient's geometry may not be significant enough to benefit from a new treatment plan.

In the current ART setup, for each treatment fraction (or every m fractions) a kV or cone beam CT (CBCT) is taken, and the current patient geometry is analyzed by visual inspection. Based on knowledge and assessment of the situation, the staff then decides if the patient needs a new re-plan or if the current re-plan is good enough. This manual decision is not always straight-forward, and may present many grey areas. Accordingly, different staffs facing the same scenario may come to different conclusions as to whether to perform a re-plan or not.

In one or more embodiments described herein, an apparatus is provided to determine, or to assist a user to determine, whether re-planning of a treatment is desirable or not.

SUMMARY

An apparatus for use in a treatment process that involves a treatment machine having an energy source, includes: one or more input communicatively coupled to one or more medium storing current treatment plan data and a current image of a patient, the one or more input configured to obtain the current treatment plan data and the current image of the patient, wherein the current treatment plan data is for processing by the treatment machine to treat the patient; and a re-planning decision processor configured to determine a re-plan information based at least in part on the current treatment plan data, the current image, and a re-plan triggering model, wherein the re-plan triggering model is based on previous treatment plan data and previous image(s), and wherein the re-plan information indicates a recommendation regarding treatment re-planning; wherein the re-planning decision processor is configured to output the re-plan information.

Optionally, the current treatment plan data comprises machine parameters for operating the treatment machine for the patient.

Optionally, the apparatus is also configured to obtain an input by the user, and wherein the re-planning decision processor is configured to determine the re-plan information also based on the input by the user.

Optionally, the input comprises one or more criteria prescribing when re-planning should be performed.

Optionally, the re-planning decision processor is configured to output the re-plan information automatically.

Optionally, the current treatment plan data comprises a CT image, a dose matrix, or both, for the patient.

Optionally, the previous treatment plan data comprises a previous CT image, a previous dose matrix, or both, for the patient or for another patient.

Optionally, the previous image(s) comprises a series of kV or CBCT images obtained at respective previous treatment times.

Optionally, the previous image(s) comprises a series of images obtained at respective previous treatment times, and wherein the apparatus further comprises a database storing the series of images in association with respective time stamps.

Optionally, the apparatus further includes a trigger detector configured to discover previously undetected trigger(s) of re-planning.

Optionally, the trigger detector is configured to discover the previously undetected trigger(s) by performing data mining to find out feature(s) that triggered the re-planning.

Optionally, the re-planning decision processor is configured to determine the re-plan information based on a similarity function.

Optionally, the re-plan information indicates one of the following three items: re-plan being recommended, no re-plan being recommended, need for re-plan being uncertain.

Optionally, the re-planning decision processor is configured to determine the re-plan information based on one or more parameters satisfying one or more criteria that include threshold values.

Optionally, the re-planning decision processor is configured to obtain transformation function that translates a kV or CBCT image to a synthetic CT image.

Optionally, the re-planning decision processor is configured to determine the re-plan information based on one or more parameters, wherein the one or more parameters comprise a time difference, a deviation of an anatomical feature in a certain direction, a certain deformation in an image, tumor size difference, tumor shift, a difference between an accumulated dose and an expected dose, or any combination of the foregoing.

Optionally, the re-planning decision processor is configured to determine the re-plan information based on a parameter obtained by a machine learning algorithm.

Optionally, the re-planning decision processor is configured to determine a transformation between the current image of the patient and a planning image for the patient, and determine whether the transformation satisfies a criterion of the re-plan triggering model.

Optionally, the previous treatment plan data comprises a previous planning image for another patient, wherein the previous image(s) comprises a previous treatment time image for the other patient, and wherein the criterion is based on a transformation between the previous planning image for the other patient and the previous treatment time image for the other patient.

Optionally, the re-planning decision processor is configured to output the re-plan information for reducing a burden, or for obviating a need, for a user of the apparatus to manually decide whether the treatment re-planning is desirable or not.

A processor-implemented method includes: establishing communication with one or more medium storing current treatment plan data and a current image of a patient; obtaining, via one or more input, the current treatment plan data and the current image of the patient from the one or more medium, wherein the current treatment plan data is for processing by a treatment machine to treat the patient; determining, using a re-planning decision processor, a re-plan information based at least in part on the current treatment plan data, the current image, and a re-plan triggering model, wherein the re-plan triggering model is based on previous treatment plan data and previous image(s), and wherein the re-plan information indicates a recommendation regarding treatment re-planning; and outputting, by the re-planning decision processor, the re-plan information.

Optionally, the re-plan information is outputted for reducing a burden, or for obviating a need, for a user to manually decide whether the treatment re-planning is desirable or not.

Other and further aspects and features will be evident from reading the following detailed description.

BRIEF DESCRIPTION OF THE DRAWINGS

The drawings illustrate the design and utility of various features described herein, in which similar elements are referred to by common reference numerals. These drawings are not necessarily drawn to scale. In order to better appreciate how the above-recited and other advantages and objects are obtained, a more particular description will be rendered, which are illustrated in the accompanying drawings. These drawings depict only exemplary features and are not therefore to be considered limiting in the scope of the claims.

DETAILED DESCRIPTION

Figure 1:
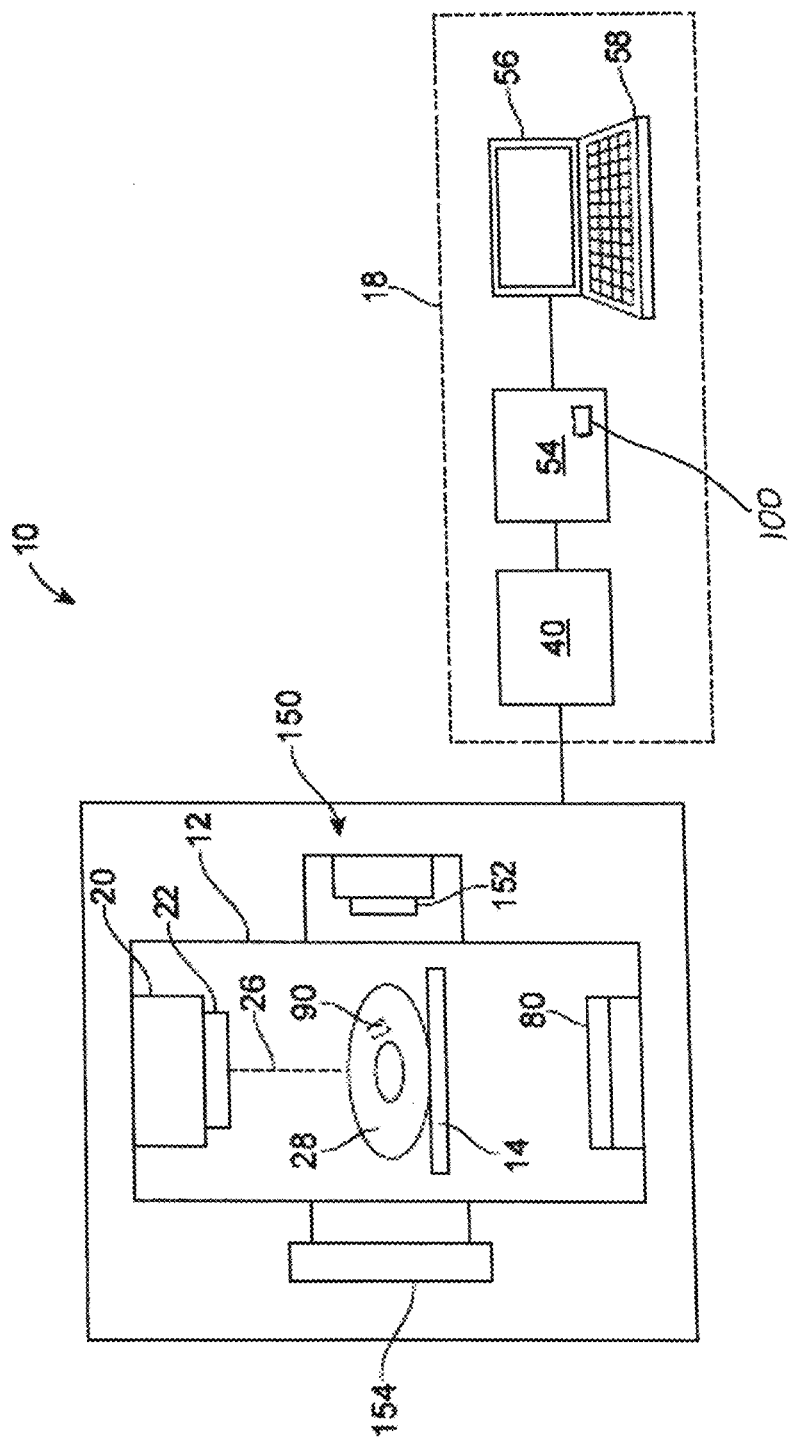
FIG. 1 illustrates a medical system that may include, or may be used with, a re-plan decision processor.

Various features are described hereinafter with reference to the figures. It should be noted that the figures are not drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated, or if not so explicitly described.

FIG. 1 illustrates a radiation system 10. The system 10 is a treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator 22 may be configured to adjust a cross sectional shape of the beam 26. The radiation source 20 can be configured to generate a cone beam, a fan beam, or other types of radiation beams in different embodiments.

As shown in the figure, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic energy for imaging purpose. In further embodiments, the system 10 may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processing unit 54. In some cases, the control 40 may also control the collimator system 22 and the position of the patient support 14. Although the control 40 is shown as a separate component from the gantry 12 and the processor 54, in alternative embodiments, the control 40 can be a part of the gantry 12 or the processing unit 54.

In the illustrated embodiments, the system 10 also includes an imaging device 150 having an imaging source 150 and an imager 154. The imaging device 150 is configured to obtain one or more images of an internal part of the patient 28. The image(s) obtained by the imaging device 150 may be used to monitor a position of the patient 28. In some cases, the imaging device 150 may be configured to obtain images of an internal fiducial 90 of the patient 28. The internal fiducial 90 may be an internal structure inside the patient 28. In some embodiments, the internal structure may move in correspondence (e.g., in sync) with a target of the patient 28 that is desired to be treated. In such cases, the internal structure may be used as a surrogate for determining a position and/or movement of the target during treatment of the patient 28, and motion management based on the surrogate may be employed in some cases. Thus, the internal fiducial 90 may be imaged by the imaging device 150 (or radiation source 20 and imager 80) that functions as a position monitoring system during a treatment of the patient 28. By means of non-limiting examples, the internal fiducial 90 may be an anatomical surrogate, such as bony structure, a vessel, a natural calcification, or any other items in a body.

In some embodiments, the imaging device 150 may be a x-ray device. In such cases, the imaging source 150 comprises a radiation source. In other embodiments, the imaging device 150 may have other configurations, and may be configured to generate images using other imaging techniques. For example, in other embodiments, the imaging device 150 may be an ultrasound imaging device, a MRI device, a tomosynthesis imaging device, or any of other types of imaging devices. Also, in the above embodiments, the imaging device 150 is illustrated as being integrated with the treatment machine. In other embodiments, the imaging device 150 may be a separate device that is separate from the treatment machine. In addition, in some embodiments, the imaging device 150 may be a room-based imaging system or a couch based imaging system. In either case, the imaging device 150 may provide any form of imaging, such as x-ray imaging, ultrasound imaging, MRI, etc. Furthermore, in other embodiments, the imaging device 150 may provide in-line imaging in the sense that it may be configured to acquire images along the same direction as the treatment beam. For example, a dual-energy source may be provided to provide imaging energy for generating an image, and to provide treatment energy to treat a patient along the same direction. In still further embodiments, the imaging device 150 may be configured to provide dual energy imaging and any form of energy-resolved imaging to increase contrast in x-ray images. For example, a first part of an image may be generated using a first energy, and a second part (e.g., a more relevant part that includes a target) of the same image may be generated using a second energy that is higher than the first energy. As a result, the second part of the image will have higher contrast compared to the first part. However, the overall dose involved in generating the whole image may be reduced compared to the situation in which the entire image is generated using the second energy.

Before the system 10 is used to treat the patient 28, a treatment plan is first determined for the patient 28. For example, a technician may obtain a treatment plan image of the patient 28, and may process the treatment plan image to create the treatment plan. By means of non-limiting examples, the treatment plan image may be a CT image, a PET-CT image, a SPECT-CT image, a x-ray image, an ultrasound image, a MRI image, a tomosynthesis image, etc. When creating the treatment plan, a treatment plan software may be utilized to assist the technician to create the treatment plan. For example, the technician may use the treatment plan software to delineate anatomical structures (target and critical organs) in the patient 28, and determine different beam delivery angles for delivering treatment energies towards the target while minimizing delivery of the energies to the critical organs. The user may also use the treatment plan software to create constraints (e.g., minimum dose to be delivered to the target, maximum allowable dose for critical organs, etc.) for the treatment planning. The treatment plan may be stored as an electronic file, and may be retrieved by the system 10 later.

On the day of the treatment, the system 10 retrieves the stored treatment plan (e.g., from a medium), and processes the treatment plan to deliver treatment energies towards the target in the patient 28. For example, a processor of the system 10 may electronically process the treatment plan to activate one or more components of the system 10 to deliver the treatment energy. The processor of the system 10 may cause the gantry 12 to rotate to a certain gantry angle prescribed by the treatment plan, and to deliver certain amount of treatment energy from the gantry angle towards the target in the patient 28. The processor of the system 10 may also control the collimator 22 to shape the beam 26 while the energy source 20 is at the gantry angle. The treatment plan may prescribe that treatment energies be delivered from multiple gantry angles. Also, the treatment plan may prescribe that the patient be treated multiple times on multiple days.

The radian treatment may include multiple fractions, and it is desirable that the radiation is delivered to the correct spot in all of the fractions. However, the daily situation at the time of treatment delivery might differ considerably from the situation predicted in the treatment plan, due to, for examples, internal organ movement (e.g., bladder filling, bowel movement, etc.), patient weight loss, tumor shrinkage, etc. In certain occasions, if the difference between the actual situation at the time of treatment delivery and the predicted situation in the treatment plan is too great, the goal of the treatment may no longer be met. In such cases, a new treatment plan is needed. In one implementation, for each treatment fraction (or every m fractions) a kV or cone beam CT (CBCT) is taken, and the current patient geometry is analyzed by visual inspection. Based on knowledge and assessment of the situation, the staff then decides if the patient needs a new re-plan or if the current plan is good enough. This manual decision is not always straight-forward, and may present many grey areas. Accordingly, it is not always clear when a new treatment plan is needed, and different staffs facing the same scenario may come to different conclusions as to whether to perform a re-plan or not. Also, performing a new plan for every treatment fraction is not always desirable as it is a time consuming task for both staff and patient. Moreover, in some cases, the patient geometry has not changed sufficiently to justify a determination of a new treatment plan.

As shown in FIG. 1, in accordance with some embodiments, the system 10 includes a re-plan decision processor 100 configured to assist a technician in determining whether treatment re-planning (to obtain a new treatment plan) is desirable or not. The re-plan decision processor 100 is illustrated as a part of the processing unit 54 in the example. In other embodiments, the re-plan decision processor 100 may be separate from the processing unit 54. For example, the re-plan decision processor 100 may be communicatively coupled to the processing unit 54, or may be completely independent of the processing unit 54 (e.g., the re-plan decision processor 100 may not be communicatively coupled to the processing unit 54). In some cases, the re-plan decision processor 100 may be implemented as a part of a treatment planning module, as a part of a control for operating the treatment system 10, or as a part of a separate monitoring system for monitoring operation condition of the treatment system 10.

Figure 2:
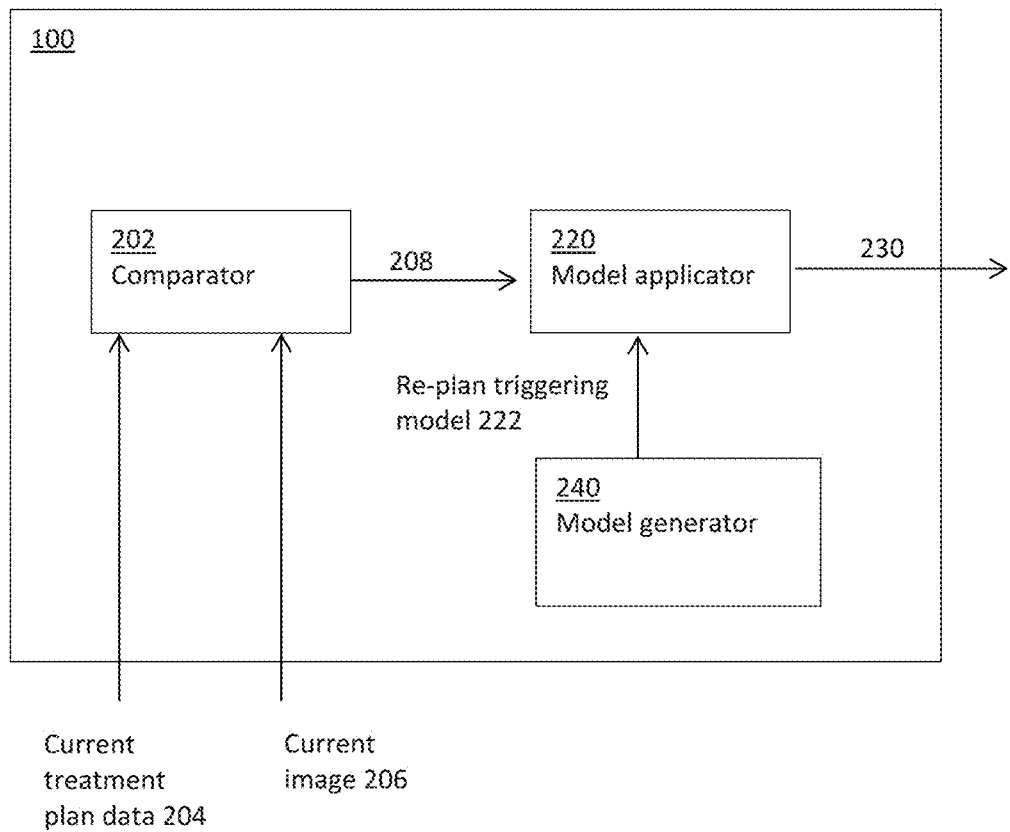
FIG. 2 illustrates an example of the re-plan decision processor of FIG. 1.

FIG. 2 illustrates an example of the re-plan decision processor 100. As shown in the figure, the re-plan decision processor 100 includes a comparator 202 configured to obtain current treatment plan data 204 and a current image 206, and to compare the treatment plan data 204 with the current image 206 to obtain a comparison result 208. The apparatus 200 also includes a model applicator 220 configured to apply a re-plan triggering model 222 to process the comparison result 208 to determine re-plan information 230. In the illustrated example, the re-pan decision processor 100 includes a model generator 240 configured to determine the re-plan triggering model 222. In other embodiments, the model generator 240 may be separate from the re-plan decision processor 100. The current treatment plan data 204 may be a treatment plan image (such as a kv image, a CT image, a PET-CT image, a SPECT-CT image, a x-ray image, an ultrasound image, a MRI image, a tomosynthesis image, etc.) obtained for use to create a treatment plan. Alternatively, or additionally, the current treatment plan data 204 may be one or more parameters/data involved in a treatment of the patient, or in a treatment planning for the patient. The current image 206 of the patient may be any image obtained during the day of the treatment, such as an image obtained while the patient is supported on a patient support next to the treatment machine. The current image 206 may be a kv image, a CT image, a PET-CT image, a SPECT-CT image, a x-ray image, an ultrasound image, a MRI image, a tomosynthesis image, etc. The comparator 202 may be configured to compare a certain feature in the treatment plan image to a certain feature in the current image.

Alternatively, or additionally, the comparator 202 may be configured to compare a treatment plan parameter with a current patient data. The treatment plan parameter may be any information involved in a planned treatment for the patient. For examples, the treatment plan parameter may be a weight of a patient, a planned dose for the patient, or any of other information, that was determined for the treatment plan. The current patient data may be a current weight of the patient, a current dose delivered to the patient, or any of other information obtained during the day of the treatment.

In some embodiments, the re-planning decision processor 100 is configured to determine the re-plan information 230 based on one or more parameters, wherein the one or more parameters comprise a time difference, a deviation of an anatomical feature in a certain direction, a certain deformation in an image, a tumor size difference, tumor shift, a difference between an accumulated dose and an expected dose, or any combination of the foregoing.

The re-plan information 230 may be (1) re-plan being recommended, or (2) no re-plan being recommended. In other cases, the re-plan information 230 may be one of (1) re-plan being recommended, or (2) no re-plan being recommended, and (3) need for re-plan being uncertain.

In some embodiments, the re-planning decision processor 100 is configured to output the re-plan information 230 automatically. For example, in response to a certain detected event, the re-planning decision processor 100 may output the re-plan information 230 automatically without any user's input. Alternatively, the outputting of the re-plan information 230 may be performed by the re-planning decision processor 100 in response to a user's request.

Figure 3:
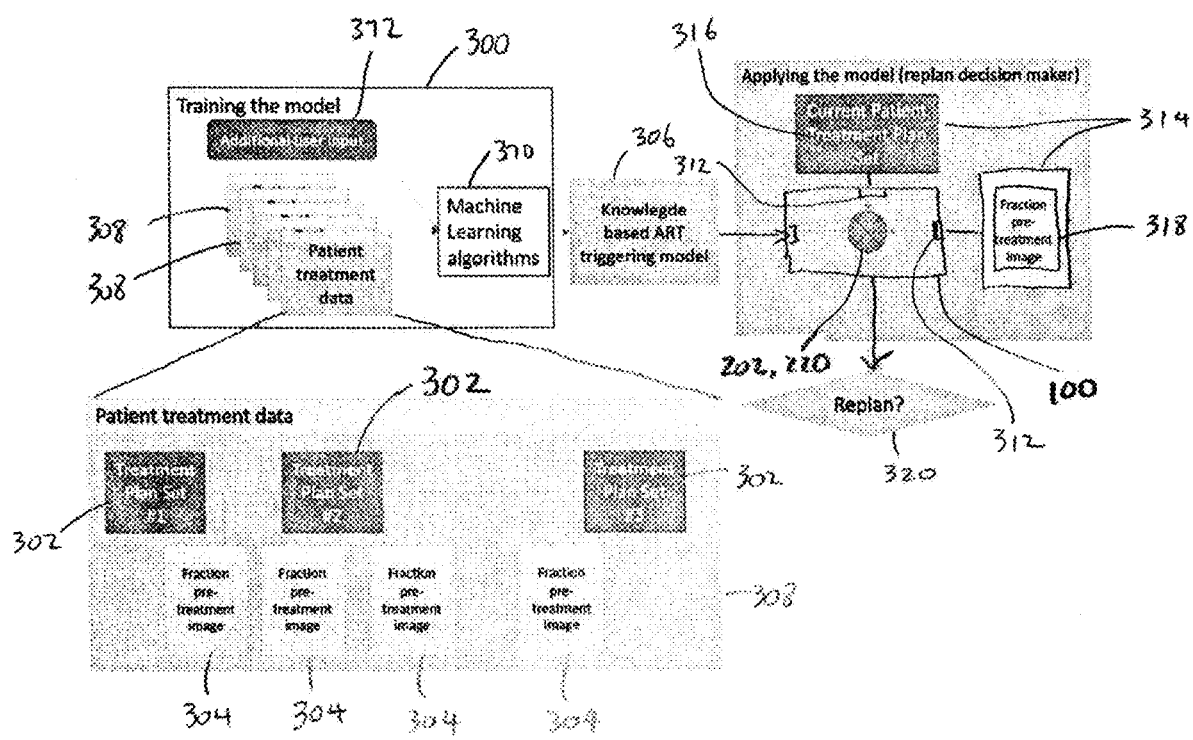
FIG. 3 illustrates information flow involved with the use of the re-plan decision processor of FIG. 1.

FIG. 3 illustrates information flow involved with the use of the re-plan decision processor 100 of FIG. 1 and FIG. 2. As shown in the figure, a model generator 300 is configured to obtain previous treatment plan data 302 and previous image(s) 304, and process the previous treatment plan data 302 and previous image(s) 304 to determine a re-plan triggering model 306, and/or to determine parameters for the re-plan triggering model 306. The model generator 300 may be an example of the model generator 240 of FIG. 2. The re-plan triggering model 306 may be an example of the re-plan triggering model 222 of FIG. 2. Returning to FIG. 3, in some embodiments, there may be multiple sets 308 of patient treatment data for respective different patients, with each set 308 having a plurality of previous treatment plan data 302 and previous images 304 for a respective one of the patients. In some cases, the previous images 304 comprise a series of kV or CBCT images obtained at respective previous treatment times. In other cases, the previous images 304 may be any of other types of images, such as MRI images, PET images, tomosynthesis images, etc. The previous images 304 may be stored in a database in association with respective time stamps. Each previous treatment plan data 302 may include a previous CT image, a previous dose matrix, or both, for the patient 28 or for another patient. Each previous treatment plan data 302 may also include other parameters, such as patient weights, dose information, etc. Each previous treatment plan data 302 may be stored in a database in association with respective time stamps. The time stamps are advantageous because they allow the model generator 300 to piece together a time line indicating a chronological order of the previous treatment plan data 302 and the previous images 304 for each of the patients.

In some embodiments, for at least one of the previous patients, the model generator 300 may be configured to determine a transformation between a previous treatment plan image (e.g., a CT image), and a previous image 304 that is subsequent to the time of the treatment plan image. The model generator 300 then registers the transformation with the previous re-plan decision. For example, if treatment re-plan was performed after the previous image 304 was obtained, the model generator 300 then registers the associated transformation with the re-plan decision (e.g., "re-plan performed"). During a previous course of treatment for a certain patient, there may be multiple treatment plan data (with respective CT images), and also multiple previous images 304 that were obtained between the times of the treatment plan data. For example, consider the following sequence of events for a certain patient who was previously treated:

Plan 1 (w/CT1), image 1, image 2, Plan 2 (w/CT2), image 3 In the above example, an initial treatment plan (Plan 1) was created for a certain patient. The plan 1 includes a corresponding CT image (CT1) that was used to create Plan 1. Subsequently, image 1 was obtained for the patient. Such may be performed during a treatment session (i.e., before delivery of treatment energy) to confirm certain anatomical geometry of the patient (e.g., that the geometry in image 1 does not deviate from CT1 by more than a certain threshold). Once the anatomical geometry of the patient was confirmed, treatment energy was then delivered to the patient based on Plan 1 (i.e., there was no re-plan performed immediately after image 1 was taken). Later, image 2 was taken to check the anatomical geometry of the patient. This may be performed during the same treatment session, or during a different treatment session (e.g., treatment session on a different day). Due to a certain change in the anatomical geometry of the patient being treated (e.g., the geometry in the image 2 may have a feature that differ from CT1 by more than a certain threshold), the technician determined that a new treatment plan was needed. Accordingly, a re-plan was performed to create a new treatment plan (Plan 2). The plan 2 includes a corresponding CT image (CT2) that was used to create Plan 2. Subsequently, image 3 was obtained for the patient. Such may be performed before delivery of treatment energy to confirm certain anatomical geometry of the patient (e.g., that the geometry in image 3 does not deviate from CT2 by more than a certain threshold). Once the anatomical geometry of the patient was confirmed, treatment energy was then delivered to the patient based on Plan 2.

Accordingly, by observing how anatomical features changed over time for a particular patient, and how those changes correlate with previous re-plan decisions, the model generator 300 may create a re-plan triggering model 306 that is knowledge based. In the above example, the model generator 300 may associate image changes with re-plan decisions, as follow:

Change between CT1 (e.g., a cross section of CT1) and image 1=>no re-plan

Change between CT1 (e.g., a cross section of CT1) and image 2=>re-plan

Change between CT2 (e.g., a cross section of CT2) and image 3=>no re-plan In the above example, a change between treatment plan image (e.g., CT image) and pre-treatment image may be a change of dimension of a particular tissue structure in a certain direction, a change in position of a particular tissue structure in a certain direction, a change in an area of a particular tissue structure as it appears in a two-dimensional image, a characteristic of a transformation between the cross section of the CT image and the pre-treatment image, etc. In some embodiments, the model generator 300 may be configured (e.g., programmed) to look for the particular feature (e.g., dimension, position, area, etc.) for which the change occurred, wherein the particular feature may be prescribed by a user. Then the model generator 300 creates the association between the detected change in the particular prescribed feature and the re-plan decision (e.g., no re-plan, or re-plan).

In some embodiments, the model generator 300 may be implemented as a part of the re-plan decision processor 100. In other embodiments, the model generator 300 may be separate from the re-plan decision processor 100.

Also, in some embodiments, the re-plan triggering model 306 may be stored in a non-transitory medium in the re-plan decision processor 100. In other embodiments, the re-plan triggering model 306 may be stored in a non-transitory medium (e.g., database) that is separate from the re-plan decision processor 100. In such cases, the re-plan decision processor 100 is configured to communicate with the non-transitory medium for obtaining the triggering model 306 from the non-transitory medium.

In the illustrated embodiments, the model generator 300 may include a machine learning module 370 for determining the re-plan triggering model 306. The machine learning module 370 is configured to obtain the previous treatment plan data 302 and the previous image(s) 304, and analyze the previous treatment plan data 302 and the previous image(s) 304 to determine the re-plan triggering model 306. In one implementation, the machine learning module 370 is configured to determine a change in one or more feature(s) associated with the previous images 304, and correlate such change with previous re-plan decisions (e.g., re-plan performed, or re-plan not performed). The one or more feature(s) associated with the previous images 304 may be a shape of a target, a dimension of a target, a shape of critical organ, a dimension of critical organ, dose value, or any combination of the foregoing. Alternatively or additionally, the machine learning module 370 may be configured to determine a change in other parameter(s) associated with previous treatment(s) of other patient(s). For example, the machine learning module 370 may be configured to determine a change in a patient's weight, and correlate such change with previous re-plan decisions. Accordingly, in some embodiments, the re-planning decision processor 100 may be configured to determine the re-plan information based on a parameter obtained by the machine learning algorithm 370.

In some embodiments, the model generator 300 is configured to receive a user input 372, and process the user input 372 together with the previous treatment plan data 302 and the previous image(s) 304 to determine the re-plan triggering model 306 and/or parameters for the re-plan triggering model 306. For example, the user may input a command instructing the model generator 300 (e.g., the machine learning module 370 of the model generator 300) to look for the dimensions (e.g., along a certain direction) of the targets in all of the previous images. In other embodiments, the model generator 300 may be configured to determine the re-plan triggering model 306 without any user input.

Alternatively, or additionally, the user input 372 may include one or more criteria prescribing the condition(s) upon which re-planning should be performed. By means of non-limiting examples, the user input may prescribe that re-planning be performed for the patient 28 when a time since a last treatment for the same patient 28 has exceed a certain limit, when a change in tumor size has exceeded a certain threshold, when a change in tumor position has exceeded a certain threshold, when a difference between an accumulated dose and an expected dose has exceeded a certain limit, when a deviation of an anatomical feature in a certain direction has met a certain criteria, etc. In such cases, the re-plan decision processor 100 is configured to determine the re-plan information based on the user input 372.

In some embodiments, instead of looking for change in a particular feature defined by a user, the model generator 300 may be configured to perform data mining to discover feature(s) having changes that correlate with re-plan decisions. For example, the model generator 300 may be configured to perform pattern or trend analysis on data stored in a non-transitory medium. The stored data may be images of one or more patients, treatment data of one or more patients, and previous re-plan decisions for one or more patients.

In the above example, the type of anatomical changes for the model generator 300 to associate with previous re-plan decisions may be prescribed by a user. For example, the user may configure the model generator 300 to look for a dimensional change of a liver in a certain direction, and associate such change with the previous re-plan decisions. In other embodiments, the model generator 300 may itself be configured to discover previously undetected trigger(s) of re-planning. For example, in some embodiments, the model generator 300 may include a trigger detector configured to discover previously undetected trigger(s) of re-planning. For example, the trigger detector may be configured to discover the previously undetected trigger(s) by performing data mining to find out feature(s) that triggered the re-planning. In one implementation, the trigger detector may be configured to look for changes in multiple features associated with the anatomy, and determine if any of those changes has any correlation with the previous re-plan decisions for one or more previous patients. If the trigger detector determines that there is a correlation (e.g., a correlation that exceeds a certain threshold, such as 0.6 or higher, or more preferably 0.7 or higher, or more preferably 0.8 or higher, or more preferably 0.9 or higher) between a change in certain feature of an anatomy and a previous re-plan decision, then trigger detector may incorporate this correlation into the re-plan triggering model 306.

In some embodiments, the model generator 300 may determine the re-plan triggering model 306 based on one set 308 of the patient treatment data. In other embodiments, the model generator 300 may also perform the same analysis using other sets 308 of patient treatment data for other previous patients that have gone through previous treatments, and "learn" how changes in anatomical features affect re-plan decisions across a population of individuals. This may result in a re-plan triggering model 306 that is more robust and reliable.

As shown in FIG. 3, after the re-plan triggering model 306 is determined, it may then be used by the re-plan decision processor 100. The re-plan decision processor 100 includes one or more input 312 communicatively coupled to one or more medium 314 storing current treatment plan data 316 and a current image 318 of a patient. The current treatment plan data 316 may be an example of the current treatment plan data 204. Also, the current image 318 may be an example of the current image 206. The one or more input 312 may be configured to obtain the current treatment plan data 316 and the current image 318 of the patient. The current treatment plan data 316 is for processing by the treatment machine to treat the patient. The re-planning decision processor 100 is configured to determine a re-plan information 320 based at least in part on the current treatment plan data 316, the current image 318, and the re-plan triggering model 306, wherein the re-plan triggering model 306 is based on previous treatment plan data 302 and previous image(s) 304. The re-plan information 320 indicates a recommendation regarding treatment re-planning. The re-plan information 320 may be an example of the re-plan information 230. The re-planning decision processor 100 is also configured to output the re-plan information 320 for reducing a burden, or for obviating a need, for a user of the apparatus to manually decide whether the treatment re-planning is desirable or not.

The re-plan triggering model 306 is configured to provide one or more criteria for making a re-plan decision based on the current treatment plan data 316 and the current image 318 of the patient. The criteria may be a part of a rule for making the re-plan decision. For example, the rule with the criteria may be: perform re-plan if a weight of the patient changes by more than 15%. As another example, the rule with the criteria may be: perform re-plan if a dimensional difference of the target as it appears in the image of the current treatment plan and the current image of the patient is more than 10%. As a further example, the rule with the criteria may be: perform re-plan if a dose value in a dose image differs from that prescribed in the plan by more than 5%. In the above examples, the values 15%, 10%, 5% may be determined by the model generator 300, which derives these criteria values based on the previous treatment plan data 302, previous image(s) 304, previous patient data, or combination of the foregoing. In some cases, the model generator 300 may determine a histogram for each of the parameters, and determine a criteria value based on the histogram. For example, a histogram of dimensional change for the target may be determined, and the model generator 300 may determine from the histogram that in the past, a re-plan was always performed, or more likely than not to have been performed, when the dimensional change for the target is more than 10%. Accordingly, the model generator 300 then incorporates this criteria value (e.g., 10%) into the model 306.

When the re-plan decision processor 100 applies the model 306, the comparator 202 of the re-plan decision processor 100 compares the dimension of the target in the treatment plan image with that in the current image of the patient to obtain a comparison result. For example, the comparison result may indicate a dimensional difference of 14%. The model applicator 220 of the re-plan decision processor 100 then applies the re-plan triggering model 222 based on this result. If the dimensional difference is more than 10% as provided by the model 222, the model applicator 220 of the re-plan decision processor 100 then recommends that a re-planning be performed. In the example, because the comparison result indicates that the difference is 14%, by applying the model 222, the model applicator 220 then determines that re-plan is recommended. Accordingly, the re-planning decision processor 100 is configured to determine the re-plan information based on one or more parameters satisfying one or more criteria that include threshold values. The one or more criteria may be based on a comparison (e.g., transformation) between previous planning image for the other patient and the previous treatment time image for the other patient, as discussed. The previous planning image may be considered an example of previous patient treatment data.

In one implementation, the re-planning decision processor 100 is configured to determine a transformation between the current image 318 of the patient and a planning image 316 for the patient, and determine whether the transformation satisfies a criterion of the re-plan triggering model 306. The criterion may include one or more threshold values as discussed. Also, in some cases, the transformation may be implemented using a transformation function that translates a kV/CBCT image to a synthetic CT image, or vice versa. In another implementation, the re-planning decision processor 100 is configured to determine the re-plan information based on a similarity function. The similarity function may be configured to compare a certain feature in the current image of the patient with a corresponding feature in a treatment plan image for the patient.

Figure 4:
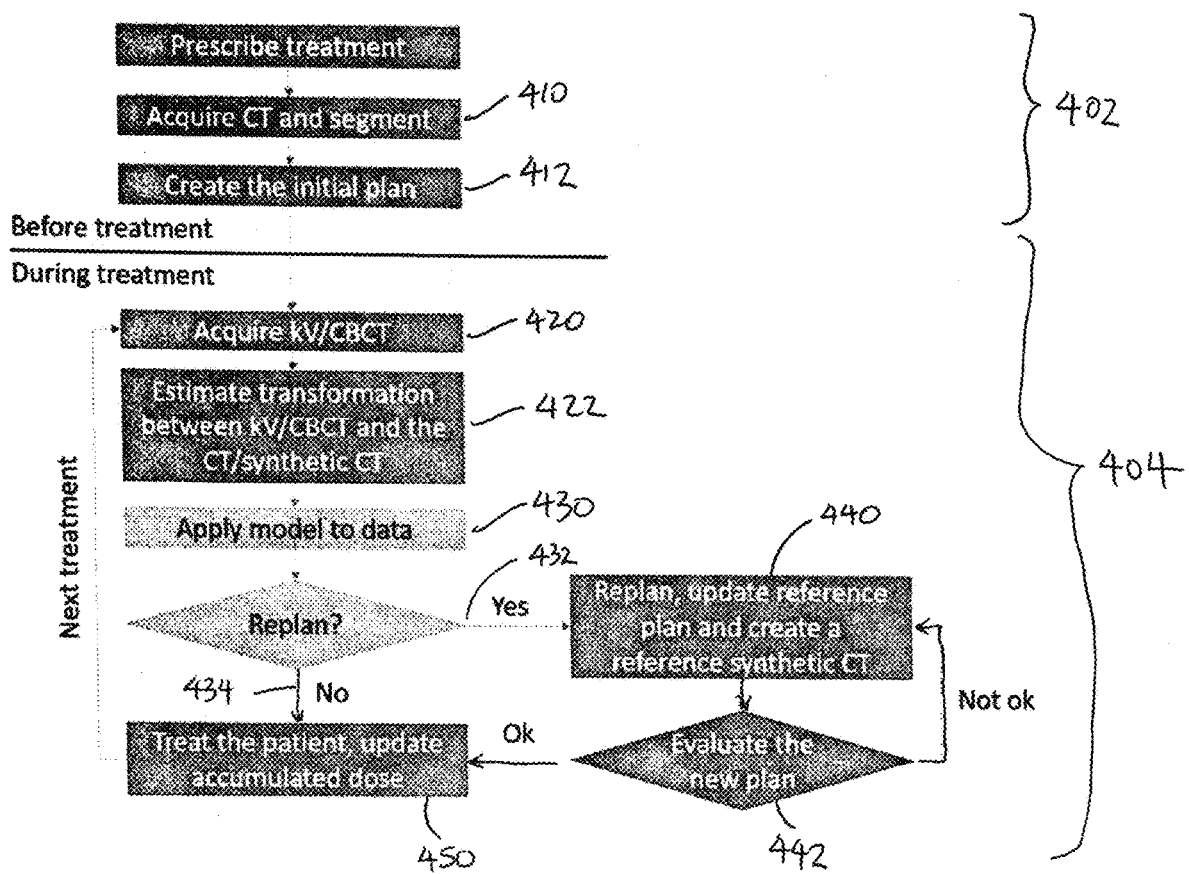
FIG. 4 illustrates a method that includes a pre-treatment process and a treatment process.

FIG. 4 illustrates a method 400 that includes a pre-treatment process 402 and a treatment process 404. During the pre-treatment process 402, a treatment plan image of the patient is obtained (item 410), and an initial treatment plan is determined based on the treatment plan image (item 412). As shown in the figure, the treatment plan image may also be segmented for allowing the initial treatment plan be determined. The treatment plan image may be a kv image, a CT image, a synthetic CT image, a x-ray image, a MRI image, a PET image, a SPECT image, a tomosynthesis image, or any of other types of image.

During the treatment process 404, the patient is imaged to obtain a current image of the patient (item 420). The current image may be a kV image, a CT image (e.g., a cone beam CT image), a x-ray image, a MRI image, a PET image, a SPECT image, a tomosynthesis image, or any of other types of image. The act of obtaining the current image may be performed by an imaging device, which generates the current image. Alternatively, the act of obtaining the current image may be performed by the re-plan decision processor 100, which receives the current image from another device, such as an imaging device, or a non-transitory medium storing the current image.

Next, the current image is compared with the treatment plan image (item 422). In some embodiments, item 422 may be performed by the re-plan decision processor 100. Also, in some embodiments, the comparison of the current image with the treatment plan image may be performed by determining a transformation between the current image and the treatment plan image. In other embodiments, item 422 may be performed by comparing a certain feature in the current image with a certain feature in the treatment plan image. The feature may be a size of a target (e.g., a dimension of the target in a certain direction), a shape of a target, a size of a critical organ (e.g., a dimension of the critical organ in a certain direction), a shape of a critical organ, etc. Also, in some embodiments, the feature being compared between the current image and the treatment plan image may correspond with that in the re-plan triggering model 306. For example, if the re-plan triggering model 306 provides a certain criteria for recommending a re-plan to be performed, and the criteria involves a change of a certain feature in an image satisfying a criteria, then in item 422, the re-plan decision processor 100 may compare that feature in the current image with that in the treatment plan image.

Next, the re-plan decision processor 100 applies the re-plan triggering model 306 based on a result of the comparison between the current image and the treatment plan image to determine whether a re-plan is recommended or not (item 430). For example, if the comparison between the current image and the treatment plan image indicates that a size difference of the target along a certain direction is 23%, and if the re-plan triggering model has a criteria for recommending re-plan if the size difference of the target along the certain direction is more than 15%, then the re-plan decision processor applies the re-plan triggering model (e.g., by comparing the 23% with the 15% criteria) to determine whether re-plan is recommended or not. In the above example, because 23%>15% provided by the re-plan triggering model 306, the re-plan decision processor 100 determines that re-plan is recommended. In other examples, instead of a size of target, other features in the current image and the treatment plan image may be compared. Also, in other embodiments, instead of comparing features in the current image and the treatment plan image, the re-plan decision processor 100 may compare other parameters. For example, the re-plan decision processor 100 may compare a weight of the patient during treatment planning and a weight of the patient during treatment session (e.g., while the patient is on the patient support next to the treatment machine, but before treatment energy is delivered). As another example, the re-plan decision processor 100 may compare planned dose in a treatment plan with a current dose already delivered to the patient (e.g., wherein the current dose may be obtained from a dose image).

If a result of item 430 indicates that re-plan is recommended, the re-plan decision processor 100 may then output re-plan information indicating that re-plan is recommended (item 432). If a user of the re-plan decision processor 100 accepts the recommendation, the user may then perform a re-planning to determine a new treatment plan (item 440). For example, the user may operate a treatment planning system to update the initial treatment plan based on the current image, or based on a new treatment plan image obtained while the patient is on the patient support next to the treatment machine. Once the new treatment plan is determined, the new treatment plan is evaluated to determine if it is suitable for execution by the treatment machine to treat the patient (item 442). If it is determined that the new treatment plan is acceptable, the new treatment plan is then executed by the treatment machine to treat the patient (item 450).

On the other hand, if a result of item 430 indicates that re-plan is not recommended, the re-plan decision processor 100 may then output re-plan information indicating that re-plan is not recommended (item 434). In such cases, the initial treatment plan is then executed by the treatment machine to treat the patient (item 450). After the patient is treated in a treatment session, the method 400 than loops back to item 420. For example, in another treatment session, which may occur on the same day or on a different day, the patient may be imaged again in item 420. The method is then repeated.

As illustrated in the above embodiments, the method 400 is advantageous because the re-plan information reduces a burden, or for obviating a need, for a user of the apparatus to manually decide whether the treatment re-planning is desirable or not.

Figure 5:
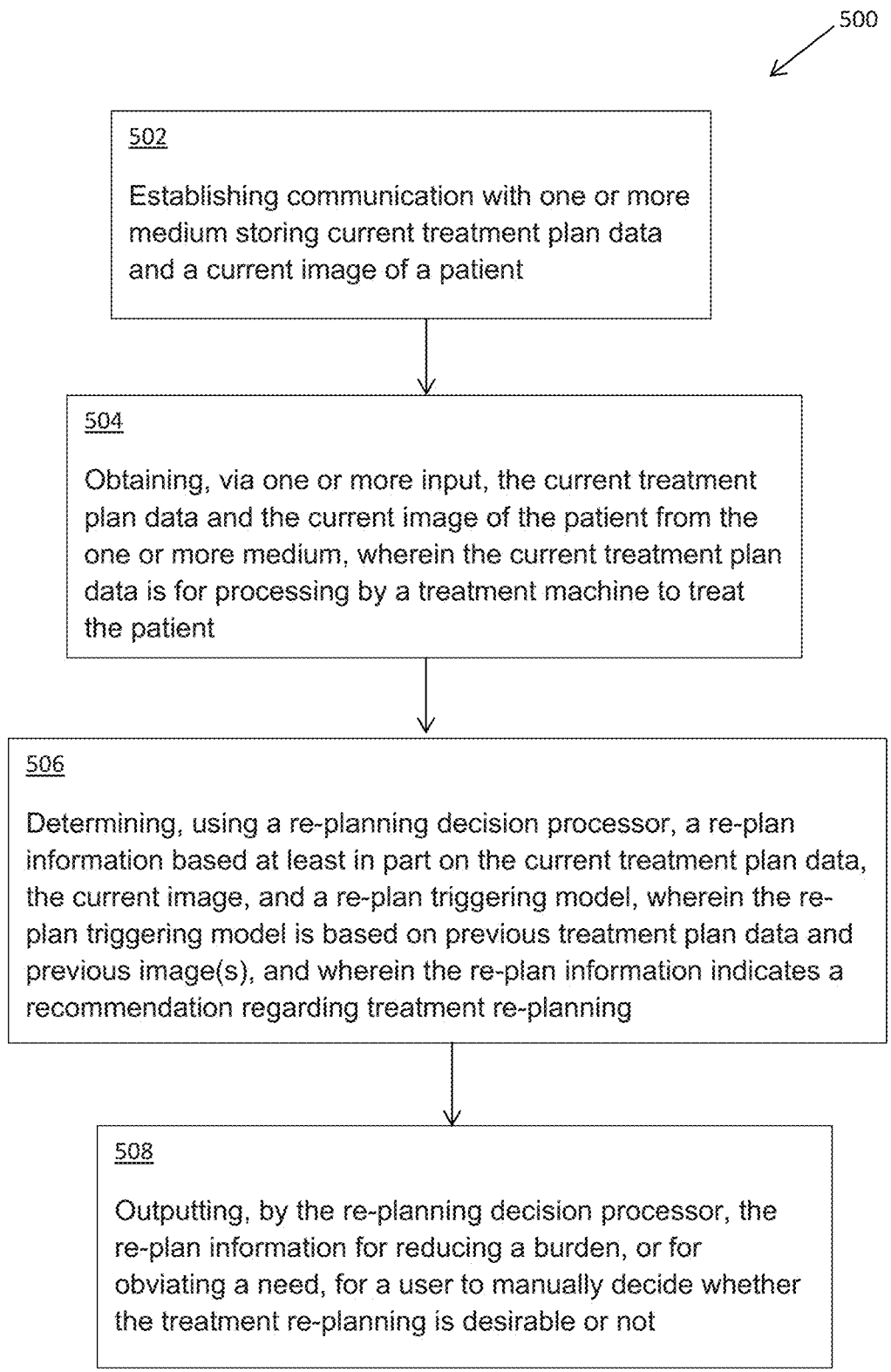
FIG. 5 illustrates a method performed by a re-plan decision processor.

FIG. 5 illustrates a method 500 performed by the re-plan decision processor 100. A processor-implemented method 500 includes establishing communication with one or more medium storing current treatment plan data and a current image of a patient (item 502). The method 500 also includes obtaining, via one or more input, the current treatment plan data and the current image of the patient from the one or more medium, wherein the current treatment plan data is for processing by a treatment machine to treat the patient (item 504). The method 500 also includes determining, using the re-planning decision processor 100, a re-plan information based at least in part on the current treatment plan data, the current image, and a re-plan triggering model, wherein the re-plan triggering model is based on previous treatment plan data and previous image(s), and wherein the re-plan information indicates a recommendation regarding treatment re-planning (item 506). The method 500 also includes outputting, by the re-planning decision processor 100, the re-plan information (item 508). In some embodiments, the re-plan information is outputted for reducing a burden, or for obviating a need, for a user to manually decide whether the treatment re-planning is desirable or not.

Figure 6:
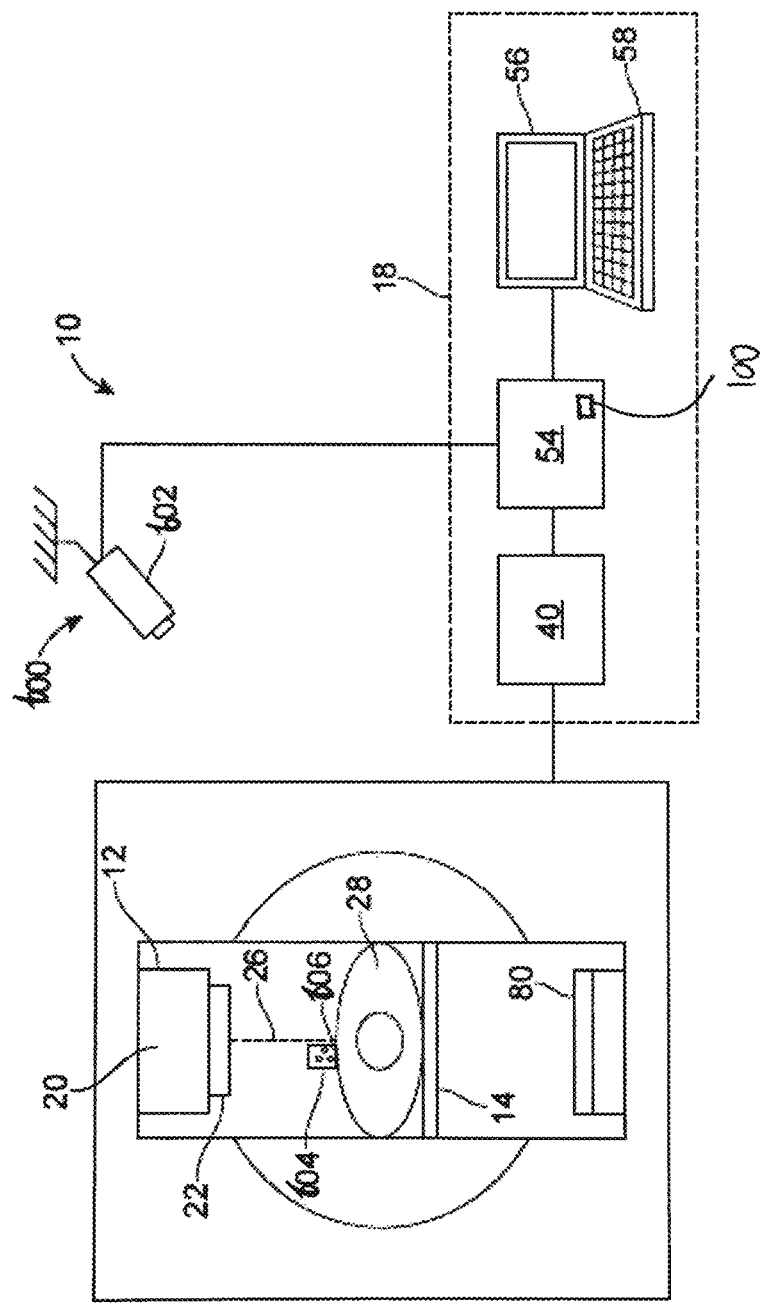
FIG. 6 illustrates another medical system that may include, or may be used with, a re-plan decision processor.

In other embodiments, instead of using an internal fiducial that is an internal part of the patient 28, the system 10 may include an external fiducial, such as a marker system, for monitoring a position of the patient 28 during treatment. FIG. 6 illustrates another system 10 that is similar to that described with reference to FIG. 1, except that the system 10 of FIG. 6 further includes a patient position monitoring system 600 that comprises a camera 602 and a marker block 604. The marker block 604 includes a plurality of markers 606, and is configured for coupling to the patient 28 during use. For example, the marker block 604 may be placed on a patient's chest, so that the marker block 604 will move correspondingly with the patient's breathing. The camera 602 is configured to view the marker block 604, and capture images of the marker block 604. The images of the marker block 604 may be processed by the processing unit 54 to determine a position of the marker block 604. The position of the marker block 604 may, in turn, be used by the processing unit 54 to determine a breathing amplitude and/or breathing phase of the patient 28.

Alternatively, instead of capturing images of the marker block 604, the camera 602 may capture the body surface of the patient and the processing unit 54 may determine a breathing amplitude and/or phase based on image of the body surface. In one implementation, a surface scanning device (e.g., a depth sensing camera) may be configured to detect a patient's surface. A processing unit may receive the depth image, and may extract a breathing signal (e.g., a breathing phase) based on the depth image. Also, in some embodiments, the processing unit may use the surface of the patient to establish a correlation between an internal target motion and external surface motion.

Figure 7:
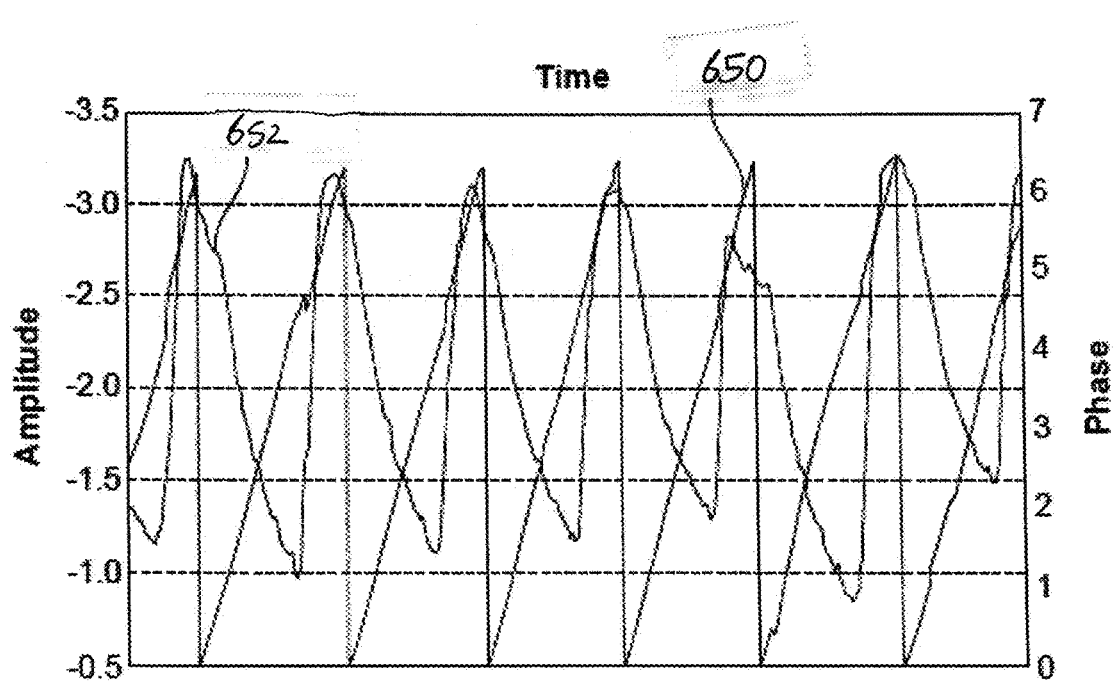
FIG. 7 illustrates an example of a phase diagram that is aligned with a corresponding amplitude/position diagram.

In one implementation, for each breathing amplitude (which may be a position of any bodily part that moves due to breathing, a position of an object coupled to such bodily part, or any signal that is associated with breathing), the processing unit 54 determines a corresponding breathing phase for the breathing amplitude. The phase of a physiological cycle represents a degree of completeness of a physiological cycle. In some embodiments, the phases of a respiratory cycle may be represented by a phase variable having values between 0° and 360°. FIG. 7 illustrates an example of a phase diagram 650 that is aligned with a corresponding amplitude/position diagram 652. Amplitude diagram 652 includes positional points of the marker block 604 or body surface determined using embodiments of the technique described herein. Each point in the amplitude diagram 652 represents a position of the marker block 604 or a bodily part at a certain point in time. In the illustrated example, a phase value of 0° (and 360°) represents a peak of an inhale state, and the phase value varies linearly between 0° and 360° in a physiological cycle. As shown in the diagram, for each point in the amplitude diagram 652 at certain point in time, a corresponding phase value at the same point in time may be obtained. Thus, for each breathing amplitude, the processing unit 54 can determine the corresponding phase of the respiratory cycle. In some embodiments, the determined phase may be considered an example of a breathing signal.

In some embodiments, when using the system 10 of FIG. 6, the radiation source 20 is rotated about the patient 28 to deliver treatment radiation from a plurality of gantry angles, for example, as in arc therapy. As treatment radiation is being delivered to the patient 28, the state of the patient 28, such as the patient's breathing states, may be monitored. In some embodiments, the processing unit 54 processes the signals from the camera 602 to determine breathing amplitudes of the patient 28, and then gates the delivery of the treatment radiation based on the amplitudes. For example, the processing unit 54 may cause the radiation source 20 to deliver radiation, or to stop a delivery of radiation, when the determined amplitude is within a prescribed amplitude range. In other embodiments, the processing unit 54 processes the signals from the camera 602 to determine respiratory phases of the patient 28, and then gates the delivery of the treatment radiation based on the respiratory phases. For example, the processing unit 54 may cause the radiation source 20 to deliver radiation, or to stop a delivery of radiation, when the determined phase is within a prescribed phase range. In further embodiments, the processing unit 54 processes the signals from the camera 602 to detect non-periodicity, and then gates the delivery of the treatment radiation based on the detection of non-periodicity. In other embodiments, instead of, or in addition to, controlling the delivery of radiation, the processing unit 54 may be configured to control the gantry 12 (e.g., stop, accelerate, or decelerate the gantry 12), and/or to position the patient support 14, based on the determined amplitude and/or phase, or detection of non-periodicity. In further embodiments, the processing unit 54 may be configured to control the gantry 12 and/or the radiation source 20 to track a movement of a target so that the treatment beam will follow the movement of the target.

During the treatment process, the processing unit 54 monitors the patient's 28 breathing, and correlates feature(s) of the breathing (such as breathing signals, breathing amplitudes, breathing phases, breathing hysteresis, etc.) with positions of internal target region that is being irradiated by the radiation beam 26. For example, based on images received from the camera 602, the processing unit 54 then determines the phase/amplitude of the breathing cycle. The phase of the breathing cycle or the amplitude is then used by the processing unit 54 to determine a position of the internal target region based on a pre-established relationship between breathing phase/amplitude and position of internal target region. In some embodiments, the relationship between the breathing phase/amplitude and target position may be pre-determined by a physician during a treatment planning process. For example, during a treatment planning process, it may be determined that when a patient is at breathing phase=40°, the corresponding position of the internal target region is at position X=45 mm, Y=23 mm, and Z=6 mm relative to the isocenter. This technique allows the treatment radiation system 10 to target delivery of radiation towards the target region based on breathing signals obtained by the system 10.

In some embodiments, the re-plan decision processor 100 may be configured to determine re-plan information based on positional information obtained using the patient position monitoring system 600. For example, the re-plan decision processor 100 may determine a metric that measures how well the position of the marker block 604 is representing the actual position of the target. If the metric is below a certain threshold, then the re-plan decision processor 100 may provide the re-plan information (e.g., recommending stopping of treatment session, and performing a re-plan). In some cases, the threshold may be determined by the model generator 240, which analyzes previous metrics and previous re-plan decisions for other patients. For example, the model generator 240 may determine that re-plan was performed for other patients when the metric was below a certain value. The model generator 240 then incorporates this value into the model 222, which is then used by the re-plan decision processor 100 to determine the re-plan information based on the current metric for the current treatment session.

Figure 8:
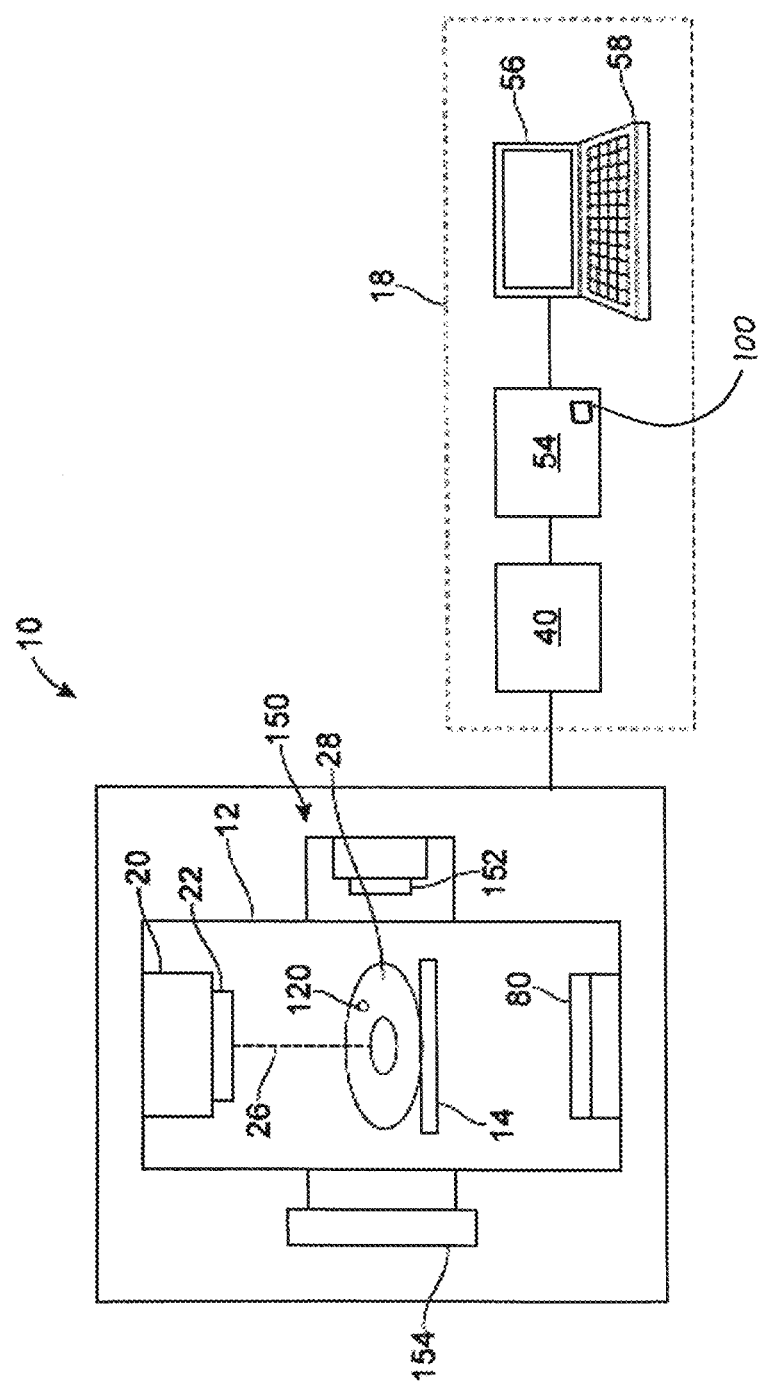
FIG. 8 illustrates another medical system that may include, or may be used with, a re-plan decision processor.

In the above embodiment of FIG. 6, the system 10 has been described as having a camera for viewing markers on a marker block to obtain motion data representing a motion of the patient 28. Alternative, reflective markers may be placed directly on the patient's surface (e.g., on the patient's skin or the patient's garment). In other embodiments, other techniques and devices may be employed to obtain motion data representing a motion of the patient 28. For example, as shown in FIG. 8, in other embodiments, one or more internal marker(s) 120 may be implanted inside the patient 28. During use, the imaging device 150 may image the marker(s) 120 to generate a sequence of images. The images form a video that captures a movement of the marker(s) 120. The marker(s) movement may correspond with a movement of a target that is desired to be treated. In such cases, the marker(s) 120 may be used as surrogate for viewing by the imaging device 150, which functions as position monitoring device for monitoring patient movement during treatment of the patient 28. Accordingly, the marker(s) 120 may function as a substitute/proxy for determining a position and/or motion of the target during treatment of the patient 28, and motion management based on the marker(s) 120 may be employed in some cases. In some embodiments, the marker(s) 120 may be implanted at the same organ that includes the target. In other embodiments, the marker(s) 120 may be implanted at the target. In further embodiments, the marker(s) may be implanted away from the target.

In some embodiments, the re-plan decision processor 100 may be configured to determine re-plan information based on positional information obtained using the marker(s) 120 and the imaging device 150. For example, the re-plan decision processor 100 may determine a metric that measures how well the position of the marker(s) 120 is representing the actual position of the target. If the metric is below a certain threshold, then the re-plan decision processor 100 may provide the re-plan information (e.g., recommending stopping of treatment session, and performing a re-plan). In some cases, the threshold may be determined by the machine learning module 270, which analyzes previous metrics and previous re-plan decisions for other patients. For example, the model generator 240 may determine that re-plan was performed for other patients when the metric was below a certain value. The model generator 240 then incorporates this value into the model 222, which is then used by the re-plan decision processor 100 to determine the re-plan information based on the current metric for the current treatment session.

Figure 9:
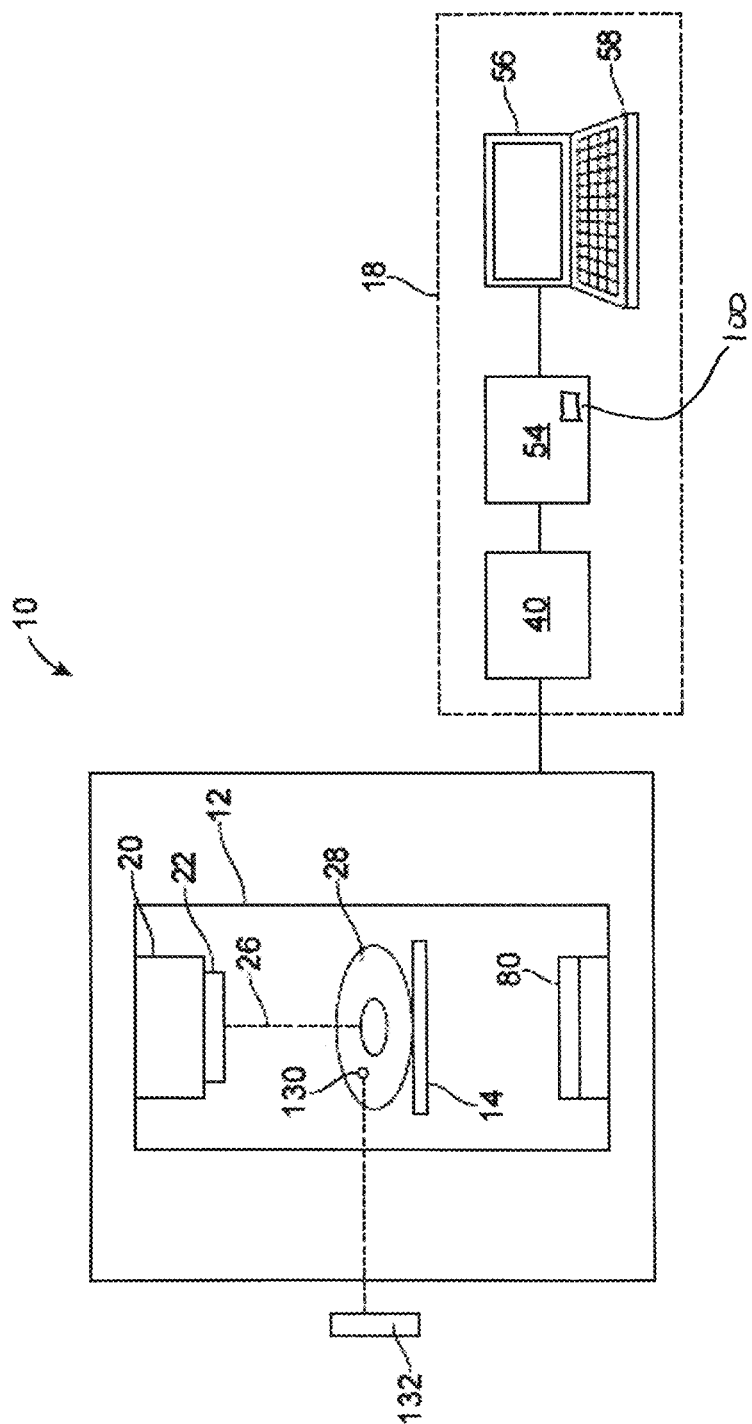
FIG. 9 illustrates another medical system that may include, or may be used with, a re-plan decision processor.

In further embodiments, the system 10 may employ internal target tracking that uses beacon(s) 130 implanted in or near the target region (e.g., tumor) along with one or more localizers 132 (FIG. 9). In one implementation, the beacon(s) may be radio frequency or electromagnetic active or passive transponder(s). In such cases, the localizer(s) 132 may be an external array antenna. During use, the transponder(s) is localized by the external array antenna transmitting query signals and processing the transponder response signals. In other cases, the beacon may be an active beacon configured to emit a signal for sensing by the localizer(s) 132. In such cases, the localizer(s) 132 may be sensor(s) configured to sense the beacon signal. The sensed signal may then be processed by a processing unit to determine a position of the beacon 130 based on triangular methods. Accordingly, the beacon(s) 130 may function as a substitute/proxy for determining a position and/or motion of the target during treatment of the patient 28, and motion management based on the beacon(s) 130 may be employed in some cases.

In some embodiments, the re-plan decision processor 100 may be configured to determine re-plan information based on positional information obtained using the beacon(s) 130 and the localizer(s) 132. For example, the re-plan decision processor 100 may determine a metric that measures how well the position of the beacon(s) 130 is representing the actual position of the target. If the metric is below a certain threshold, then the re-plan decision processor 100 may provide the re-plan information (e.g., recommending stopping of treatment session, and performing a re-plan). In some cases, the threshold may be determined by the model generator 240, which analyzes previous metrics and previous re-plan decisions for other patients. For example, the model generator 240 may determine that re-plan was performed for other patients when the metric was below a certain value. The model generator 240 then incorporates this value into the model 222, which is then used by the re-plan decision processor 100 to determine the re-plan information based on the current metric for the current treatment session.

Figure 10:
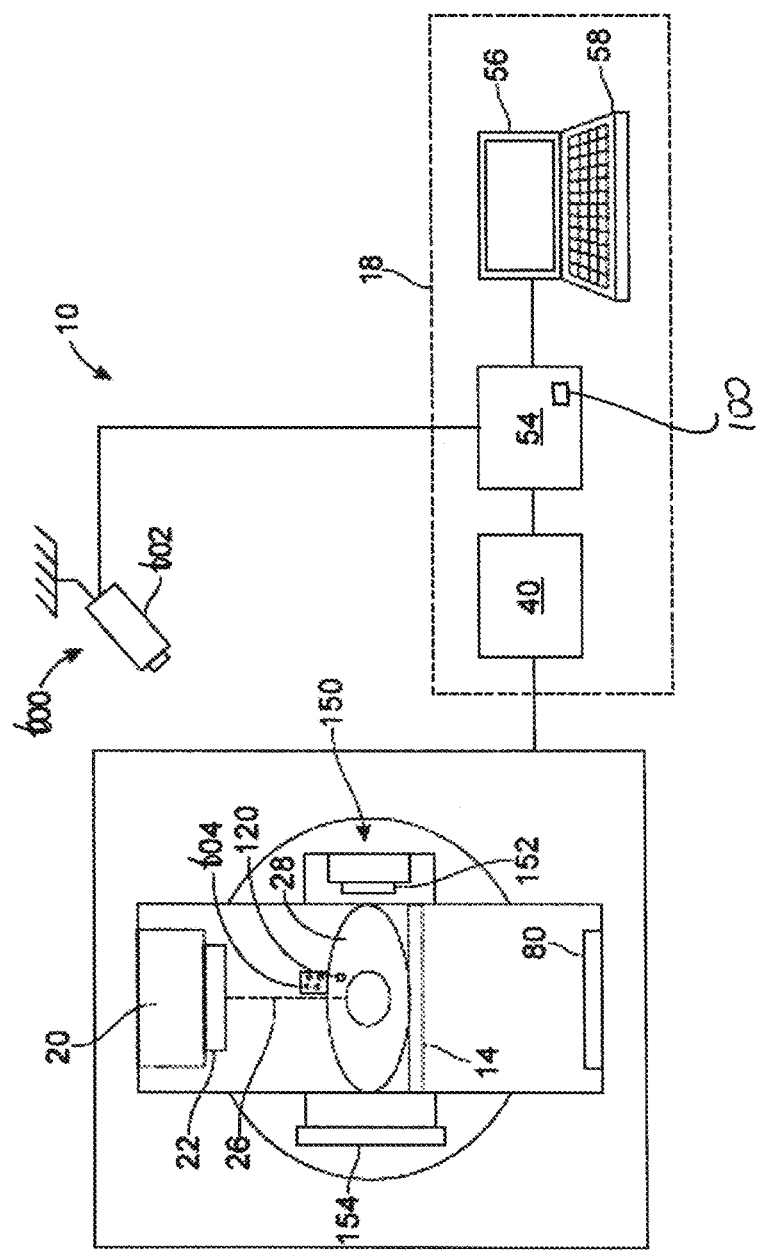
FIG. 10 illustrates another medical system that may include, or may be used with, a re-plan decision processor.

In other embodiments, the system 10 may utilize both external marker(s) and internal marker(s) for monitoring position and/or motion of the patient 28. For example, as shown in FIG. 10, the system 10 may include the patient position monitoring system 600 (having the camera 602 for viewing the marker block 604), as well as the imaging device 150 view imaging internal marker(s) 120. In other embodiments, other object(s) may be used as external marker(s), and internal marker(s). For example, in other embodiments, an anatomical surrogate inside the patient may be used as an internal marker. Also, in other embodiments, instead of using the camera 602 to detect marker block 604, a surface scanning system may be provided to detect a surface of a patient. In such cases, the surface or a feature of the detected surface may function as external marker(s). In a system in which both external and internal markers are detected, the system may be configured to determine a correlation model that correlates motion of the external marker(s) with motion of the internal marker(s).

In some embodiments, the re-plan decision processor 100 may be configured to determine re-plan information based on positional information obtained using (1) marker block 604 and/or the internal marker(s) 120. For example, the re-plan decision processor 100 may determine a metric that measures how well the position of the marker(s) 120 and/or the position of the marker block 604 is representing the actual position of the target. If the metric is below a certain threshold, then the re-plan decision processor 100 may provide the re-plan information (e.g., recommending stopping of treatment session, and performing a re-plan). In some cases, the threshold may be determined by the model generator 240, which analyzes previous metrics and previous re-plan decisions for other patients. For example, the model generator 240 may determine that re-plan was performed for other patients when the metric was below a certain value. The model generator 240 then incorporates this value into the model 222, which is then used by the re-plan decision processor 100 to determine the re-plan information based on the current metric for the current treatment session.

In other embodiments, the system 10 may include other types of devices for providing breathing information or positional information regarding a portion of the patient 28. For example, in other embodiments, the system 10 may include a strain-gauge that is coupled to the patient 28. In such cases, the strain-gauge is communicatively coupled to the processing unit 54 for providing signals that represent breathing amplitudes of the patient 28. In other embodiments, the system 10 may include a sensor coupled to the patient's mouth and/or nose for sensing the breathing of the patient. The processing unit 54 is communicatively coupled to the sensor, and receives signals from the sensor. The signals may represent the breathing amplitudes, or may be used to obtain breathing amplitudes and/or breathing phases.

In the above embodiments, the treatment system has been described as delivering radiation. In some cases, the treatment system may be configured to provide a proton beam, or other particle beams, for treating the patient. The proton beam (or other particle beam) may be considered as a form of radiation. Thus, as used in this specification, the term "radiation" is not limited to x-ray type radiation, and may include other forms of energy deliveries that "radiate" from a source.

Specialized Processing System

Figure 11:
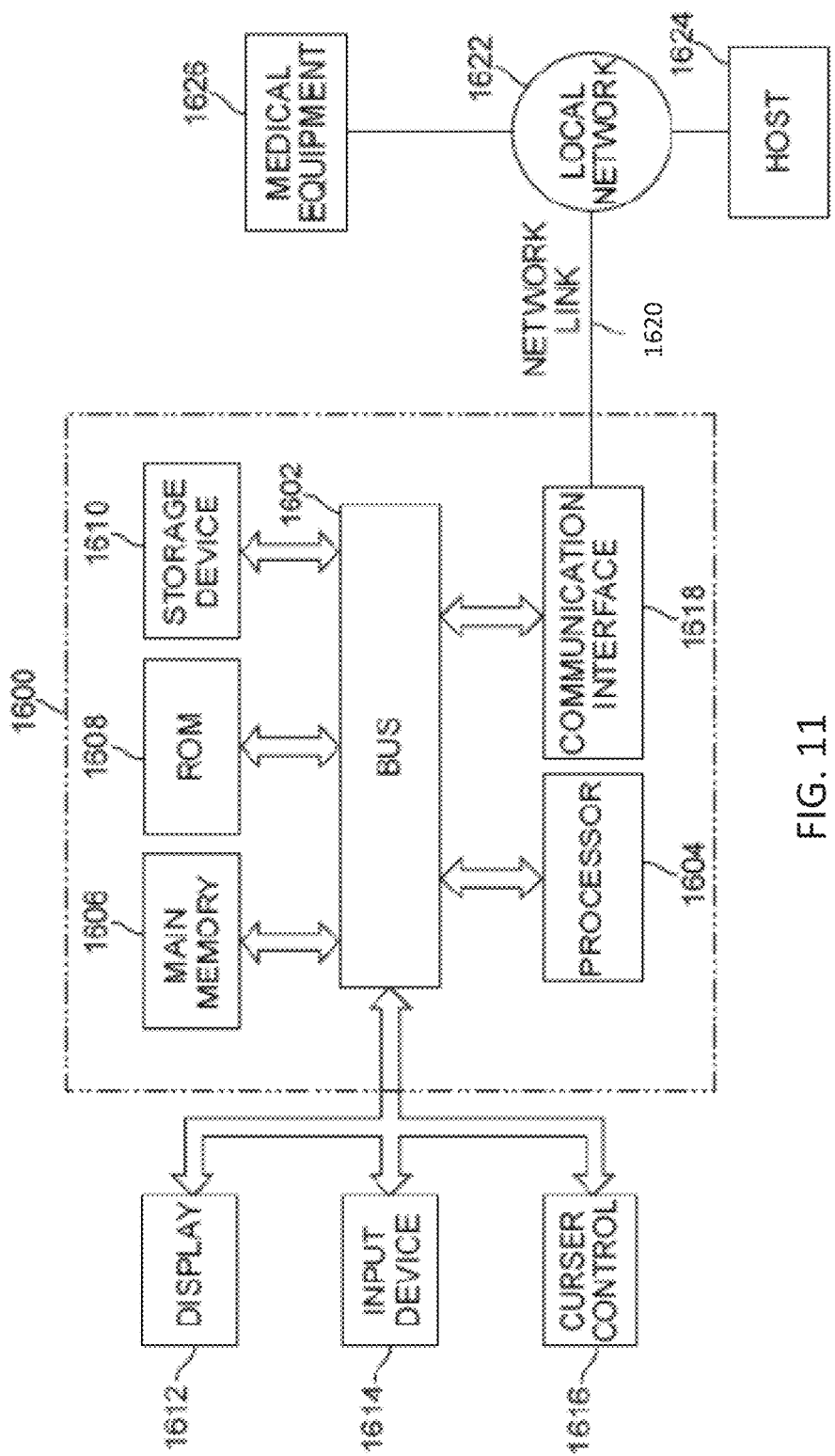
FIG. 11 is a block diagram of a specialized processing system.

FIG. 11 is a block diagram illustrating an embodiment of a specialized processing system 1600 that can be used to implement various embodiments described herein. For example, the processing system 1600 may be configured to perform any part of the method 400 of FIG. 4, or the method 500 of FIG. 5. Also, in some embodiments, the processing system 1600 may be used to implement the re-planning decision processor 100. The processing system 1600 may also be any processor described herein.

Referring to FIG. 11, the processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

The invention claimed is:

1. An apparatus for use in a treatment process that involves a treatment machine having an energy source, the apparatus comprising:
one or more input communicatively coupled to one or more medium storing current treatment plan data and a current image of a patient, the one or more input configured to obtain the current treatment plan data and the current image of the patient, wherein the current treatment plan data is for processing by the treatment machine to treat the patient; and
a re-planning decision processor configured to determine a re-plan information based at least in part on the current treatment plan data, the current image, and a re-plan triggering model, wherein the re-plan triggering model is based on previous treatment plan data and previous image(s), and wherein the re-plan information comprises a recommendation indicating whether treatment re-planning is desirable or not;
wherein the re-planning decision processor is configured to output the re-plan information; and
wherein the re-planning decision processor is configured to determine the re-plan information comprising the recommendation indicating whether treatment re-planning is desirable or not based also on one or more previous decisions on whether to perform treatment re-planning or not, wherein the one or more previous decisions are stored in the one or more medium.

2. The apparatus of claim 1, wherein the current treatment plan data comprises machine parameters for operating the treatment machine for the patient.

3. The apparatus of claim 1, wherein the apparatus is also configured to obtain an input by a user, and wherein the re-planning decision processor is configured to determine the re-plan information based on the input by the user.

4. The apparatus of claim 3, wherein the input comprises one or more criteria prescribing when re-planning should be performed.

5. The apparatus of claim 1, wherein the current treatment plan data comprises a CT image, a dose matrix, or both, for the patient.

6. The apparatus of claim 5, wherein the previous treatment plan data comprises a previous CT image, a previous dose matrix, or both, for the patient or for another patient.

7. The apparatus of claim 1, wherein the previous image(s) comprises a series of kV or CBCT images obtained at respective previous treatment times.

8. The apparatus of claim 1, wherein the previous image(s) comprises a series of images obtained at respective previous treatment times, and wherein the apparatus further comprises a database storing the series of images in association with respective time stamps.

9. An apparatus for use in a treatment process that involves a treatment machine having an energy source, the apparatus comprising:
one or more input communicatively coupled to one or more medium storing current treatment plan data and a current image of a patient, the one or more input configured to obtain the current treatment plan data and the current image of the patient, wherein the current treatment plan data is for processing by the treatment machine to treat the patient; and
a re-planning decision processor configured to determine a re-plan information based at least in part on the current treatment plan data, the current image, and a re-plan triggering model, wherein the re-plan triggering model is based on previous treatment plan data and previous image(s), and wherein the re-plan information indicates a recommendation regarding treatment re-planning;
wherein the re-planning decision processor is configured to output the re-plan information; and
wherein the apparatus further comprises a trigger detector configured to discover previously undetected trigger(s) of re-planning.

10. The apparatus of claim 9, wherein the trigger detector is configured to discover the previously undetected trigger(s) by performing data mining to find out feature(s) that triggered the re-planning.

11. The apparatus of claim 1, wherein the re-plan information indicates one of the following three items: re-plan being recommended, no re-plan being recommended, need for re-plan being uncertain.

12. The apparatus of claim 1, wherein the re-planning decision processor is configured to determine the re-plan information based on one or more parameters satisfying one or more criteria that include threshold values.

13. The apparatus of claim 1, wherein the re-planning decision processor is configured to obtain transformation function that translates a kV or CBCT image to a synthetic CT image.

14. The apparatus of claim 1, wherein the re-planning decision processor is configured to determine the re-plan information based on one or more parameters, wherein the one or more parameters comprise a time difference, a deviation of an anatomical feature in a certain direction, a certain deformation in an image, tumor size difference, tumor shift, a difference between an accumulated dose and an expected dose, or any combination of the foregoing.

15. The apparatus of claim 1, wherein the re-planning decision processor is configured to determine the re-plan information based on a parameter obtained by a machine learning algorithm.

16. The apparatus of claim 1, wherein the re-planning decision processor is configured to determine a transformation between the current image of the patient and a planning image for the patient, and determine whether the transformation satisfies a criterion of the re-plan triggering model.

17. The apparatus of claim 16, wherein the previous treatment plan data comprises a previous planning image for another patient, wherein the previous image(s) comprises a previous treatment time image for the other patient, and wherein the criterion is based on a transformation between the previous planning image for the other patient and the previous treatment time image for the other patient.

18. A processor-implemented method comprising:
establishing communication with one or more medium storing current treatment plan data and a current image of a patient;
obtaining, via one or more input, the current treatment plan data and the current image of the patient from the one or more medium, wherein the current treatment plan data is for processing by a treatment machine to treat the patient;
determining, using a re-planning decision processor, a re-plan information based at least in part on the current treatment plan data, the current image, and a re-plan triggering model, wherein the re-plan triggering model is based on previous treatment plan data and previous image(s), and wherein the re-plan information comprises a recommendation indicating whether treatment re-planning is desirable or not; and outputting, by the re-planning decision processor, the re-plan information;

wherein the re-planning decision processor is configured to determine the re-plan information comprising the recommendation indicating whether treatment re-planning is desirable or not based also on one or more previous decisions on whether to perform treatment re-planning or not, wherein the one or more previous decisions are stored in the one or more medium.

19. An apparatus for use in a treatment process that involves a treatment machine having an energy source, the apparatus comprising:

one or more input communicatively coupled to one or more medium storing current treatment plan data and a current image of a patient, the one or more input configured to obtain the current treatment plan data and the current image of the patient, wherein the current treatment plan data is for processing by the treatment machine to treat the patient; and a re-planning decision processor configured to determine a re-plan information based at least in part on the current treatment plan data, the current image, and a re-plan triggering model, wherein the re-plan triggering model is based on previous treatment plan data and previous image(s), and wherein the re-plan information comprises a recommendation indicating whether treatment re-planning is desirable or not;

wherein the re-planning decision processor is configured to output the re-plan information; and wherein the previous treatment plan data is for the patient or for another patient, and wherein the previous image(s) is for the patient or for the other patient; and wherein the re-planning decision processor is configured to determine the recommendation indicating whether treatment re-planning for the patient is desirable or not based on the previous treatment plan data and/or the previous image(s).

20. A processor-implemented method comprising:

establishing communication with one or more medium storing current treatment plan data and a current image of a patient;

obtaining, via one or more input, the current treatment plan data and the current image of the patient from the one or more medium, wherein the current treatment plan data is for processing by a treatment machine to treat the patient;

determining, using a re-planning decision processor, a re-plan information based at least in part on the current treatment plan data, the current image, and a re-plan triggering model, wherein the re-plan triggering model is based on previous treatment plan data and previous image(s), and wherein the re-plan information comprises a recommendation indicating whether treatment re-planning is desirable or not; and outputting, by the re-planning decision processor, the re-plan information;

wherein the previous treatment plan data is for the patient or for another patient, and wherein the previous image(s) is for the patient or for the other patient; and wherein the recommendation indicating whether treatment re-planning for the patient is desirable or not is determined by the re-planning decision processor based on the previous treatment plan data and/or the previous image(s).

21. An apparatus for use in a treatment process that involves a treatment machine having an energy source, the apparatus comprising:

one or more input communicatively coupled to one or more medium storing current treatment plan data and a current image of a patient, the one or more input configured to obtain the current treatment plan data and the current image of the patient, wherein the current treatment plan data is for processing by the treatment machine to treat the patient; and a re-planning decision processor configured to determine a re-plan information based at least in part on the current treatment plan data, the current image, wherein the re-plan information comprises a recommendation indicating whether treatment re-planning is desirable or not;

wherein the re-planning decision processor is configured to determine the recommendation indicating whether treatment re-planning for the patient is desirable or not based at least on (1) previous treatment plan data and/or previous image(s) for another patient stored in the one or more medium, and/or (2) a previous decision on whether to perform treatment re-planning or not stored in the one or more medium; and wherein the re-planning decision processor is configured to output the re-plan information.

* * * * *